United States Patent [19]

Szczepanski

[11] Patent Number: 4,515,626

[45] Date of Patent: May 7, 1985

[54] N-(CYCLOPROPYL-TRIAZINYL-N'-(ARYL-SULFONYL) UREAS HAVING HERBICIDAL ACTIVITY

[75] Inventor: Henry Szczepanski, Wallbach, Switzerland

[73] Assignee: Ciba Geigy Corporation, Ardsley, N.Y.

[21] Appl. No.: 535,527

[22] Filed: Sep. 26, 1983

[30] Foreign Application Priority Data

Oct. 6, 1982 [CH] Switzerland ............. 5874/82

[51] Int. Cl.³ ............... C07D 251/18; C07D 251/42; C07D 251/16; A01N 43/66
[52] U.S. Cl. ...................... 71/93; 544/211; 544/206
[58] Field of Search ............ 544/211, 206; 71/93

[56] References Cited

U.S. PATENT DOCUMENTS 3,441,560 4/1969 Zimmermann ............ 260/239.75
3,507,958 4/1970 Zimmermann ............ 424/229

FOREIGN PATENT DOCUMENTS 0009419 4/1980 European Pat. Off. .
0010560 5/1980 European Pat. Off. .

Primary Examiner—John M. Ford
Attorney, Agent, or Firm—Edward McC. Roberts; Frederick H. Rabin

[57] ABSTRACT

N-(Cyclopropyl-triazinyl- and -pyrimidinyl)-N'-arylsulfonyl ureas of the formula

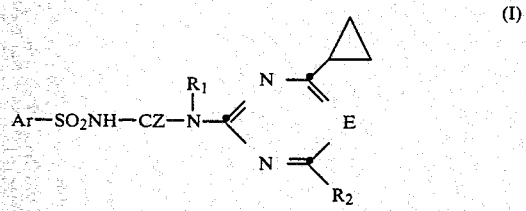

(I)

wherein Ar is a phenyl group

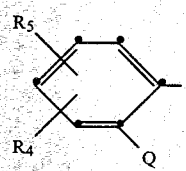

or a naphthyl group

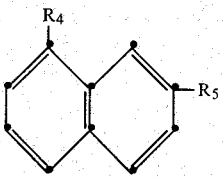

and

Q is a group X-A or $R_3$,

A is a $C_3$–$C_6$-alkynyl group, a $C_1$–$C_6$-alkyl group which is unsubstituted or substituted by halogen, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-haloalkoxy, $C_1$–$C_4$-haloalkylthio, $C_1$–$C_4$-haloalkylsulfinyl or $C_1$–$C_4$-haloalkylsulfonyl, or a $C_2$–$C_6$-alkenyl group which is unsubstituted or substituted by the groups given in the foregoing for $C_1$–$C_6$-alkyl, or A is a phenyl or benzyl group, E is the methine group or nitrogen, X is oxygen, sulfur, or a sulfinyl or sulfonyl bridge, Z is oxygen or sulfur, $R_1$ is hydrogen, $C_1$–$C_4$-alkyl or $C_1$–$C_4$-alkoxy, $R_2$ is halogen, $C_1$–$C_3$-alkyl, $C_1$–$C_3$-haloalkyl, $C_1$–$C_3$-alkoxy, $C_1$–$C_3$-haloalkoxy, amino, $C_1$–$C_3$-alkylamino, di-($C_1$–$C_3$-alkyl)amino, $C_3$–$C_6$-cycloalkyl or $C_2$–$C_6$-alkoxyalkyl, $R_3$ is hydrogen, halogen, $C_1$–$C_5$-alkyl, $C_2$–$C_5$-alkenyl, $C_1$–$C_4$-haloalkyl, or a group —X-$R_6$, —COZ$R_{11}$, —NO$_2$ or —CO-NR$_8$R$_9$, —CN, —COR$_{10}$, —NR$_1$R$_7$ or —NR$_1$-COR$_{12}$, $R_4$ is hydrogen, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, halogen, or alkoxyalkyl having at most 4 carbon atoms, $R_5$ is the same as $R_3$ but independent thereof, $R_6$ and $R_7$ are each $C_1$–$C_5$-alkyl, $C_2$–$C_5$-alkenyl or $C_2$–$C_6$-alkynyl, $R_8$ and $R_9$ independently of one another are each hydrogen, $C_1$–$C_5$-alkyl, $C_2$–$C_5$-alkenyl or $C_2$–$C_6$-alkynyl, $R_{10}$ is hydrogen, $C_1$–$C_4$-alkyl or $C_1$–$C_3$-haloalkyl, $R_{11}$ is hydrogen, $C_1$–$C_4$-alkyl, $C_1$–$C_3$-haloalkyl, $C_3$–$C_5$-alkenyl, $C_3$–$C_5$-alkynyl, phenyl or benzyl, and $R_{12}$ is the same as $R_1$ but independent thereof, and the salts of these compounds with amines, alkali metal bases or alkaline-earth metal bases or with quaternary ammonium bases, have good pre- and post-emergence-selective herbicidal and plant-growth-regulating properties.

13 Claims, No Drawings

N-(CYCLOPROPYL-TRIAZINYL-N'-(ARYLSULFONYL) UREAS HAVING HERBICIDAL ACTIVITY

The present invention relates to novel, herbicidally effective N-(cyclopropyl-triazinyl- and -pyrimidinyl)-N'-(arylsulfonyl) ureas, to processes for producing them, to compositions containing them as active ingredients, and to the use thereof for controlling weeds, especially selectively, in crops of cultivated plants, or for regulating plant growth.

The N-(cyclopropyl-triazinyl- and -pyrimidinyl)-N'-(arylsulfonyl) ureas according to the invention correspond to the general formula I

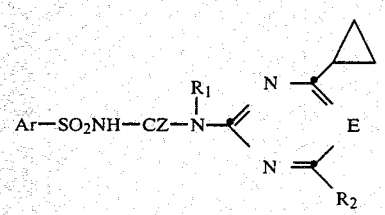

wherein Ar is a phenyl group

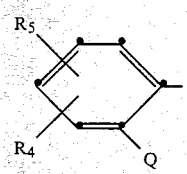

or a naphthyl group

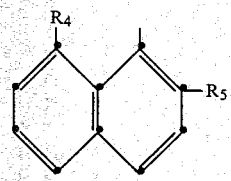

and
Q is a group X-A or $R_3$,
A is a $C_3$-$C_6$-alkynyl group, a $C_1$-$C_6$-alkyl group which is unsubstituted or substituted by halogen, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-haloalkoxy, $C_1$-$C_4$-haloalkylthio, $C_1$-$C_4$-haloalkylsulfinyl or $C_1$-$C_4$-haloalkylsulfonyl, or a $C_2$-$C_6$-alkenyl group which is unsubstituted or substituted by the groups given in the foregoing for $C_1$-$C_6$-alkyl, or A is a phenyl or benzyl group,
E is the methine group or nitrogen,
X is oxygen, sulfur, or a sulfinyl or sulfonyl bridge,
Z is oxygen or sulfur,
$R_1$ is hydrogen, $C_1$-$C_4$-alkyl or $C_1$-$C_4$-alkoxy,
$R_2$ is halogen, $C_1$-$C_3$-alkyl, $C_1$-$C_3$-haloalkyl, $C_1$-$C_3$-alkoxy, $C_1$-$C_3$-haloalkoxy, amino, $C_1$-$C_3$-alkylamino, di-($C_1$-$C_3$-alkyl)amino, $C_3$-$C_6$-cycloalkyl or $C_2$-$C_6$-alkoxyalkyl,
$R_3$ is hydrogen, halogen, $C_1$-$C_5$-alkyl, $C_2$-$C_5$-alkenyl, $C_1$-$C_4$-haloalkyl, or a group —X—$R_6$, —$COZR_{11}$, —$NO_2$ or —CO—$NR_8R_9$, —CN, —$COR_{10}$, —$NR_1R_7$ or —$NR_1$—$COR_{12}$,
$R_4$ is hydrogen, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, halogen, or alkoxyalkyl having at most 4 carbon atoms,
$R_5$ is the same as $R_3$ but independent thereof,
$R_6$ and $R_7$ are each $C_1$-$C_5$-alkyl, $C_2$-$C_5$-alkenyl or $C_2$-$C_6$-alkynyl,
$R_8$ and $R_9$ independently of one another are each hydrogen, $C_1$-$C_5$-alkyl, $C_2$-$C_5$-alkenyl or $C_2$-$C_6$-alkynyl,
$R_{10}$ is hydrogen, $C_1$-$C_4$-alkyl or $C_1$-$C_3$-haloalkyl,
$R_{11}$ is hydrogen, $C_1$-$C_4$-alkyl, $C_1$-$C_3$-haloalkyl, $C_3$-$C_5$-alkenyl, $C_3$-$C_5$-alkynyl, phenyl or benzyl, and
$R_{12}$ is the same as $R_1$ but independent thereof,
and also the salts of these compounds are included.

Urea compounds, triazine compounds and pyrimidine compounds having herbicidal activity are in general known. Arylsulfamoyl-heterocyclyl-aminocarbamoyl compounds having a herbicidal action and an action regulating plant growth have recently been described for example in the European Patent Publications Nos. 9419 and 10560.

By alkyl in the definitions is meant straight-chain or branched-chain alkyl, for example: methyl, ethyl, n-propyl, i-propyl, the four isomeric butyl groups, n-amyl, i-amyl, 2-amyl, 3-amyl, n-hexyl or i-hexyl.

By alkoxy is meant: methoxy, ethoxy, n-propyloxy, i-propyloxy and the four isomeric butyl groups, especially however methoxy, ethoxy or i-propoxy.

Examples of alkylthio are: methylthio, ethylthio, n-propylthio, i-propylthio and n-butylthio, particularly however methylthio and ethylthio.

Examples of alkenyl groups are: vinyl, allyl, isopropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, especially vinyl, allyl and 4-pentenyl.

Examples of alkylsulfinyl are: methylsulfinyl, ethylsulfinyl, n-propylsulfinyl and n-butylsulfinyl, in particular methylsulfinyl and ethylsulfinyl.

Examples of alkylsulfonyl are: methylsulfonyl, ethylsulfonyl, n-propylsulfonyl and n-butylsulfonyl, especially methylsulfonyl and ethylsulfonyl.

By halogen in the definitions as well as in haloalkyl, haloalkoxy, haloalkylsulfinyl, haloalkylsulfonyl and haloalkylthio are meant fluorine, chlorine and bromine, preferably however fluorine and chlorine.

Correspondingly, by haloalkyl or by haloalkyl moieties of the above-defined substituents are meant for example: chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, particularly chloromethyl, difluoromethyl, trifluoromethyl and trichloromethyl.

Alkynyl groups in the definitions of the above symbols are as a rule: propargyl, 2-butynyl, 3-butynyl, and also isomeric pentynyl or hexynyl groups; preferably however, the alkynyl group is propargyl or 2- or 3-butynyl.

The invention embraces also the salts which the compounds of the formula I can form with amines, alkali metal and alkaline-earth metal bases or quaternary ammonium bases.

Alkali metal hydroxides and alkaline-earth metal hydroxides to be emphasised as salt formers are hydroxides of lithium, sodium, potassium, magnesium or calcium, especially those of sodium and potassium.

Examples of amines suitable for salt formation are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, particularly ethyl-, propyl-, diethyl- or triethylamine, especially iso-propylamine and diethanolamine.

Examples of quaternary ammonium bases are in general the cations of haloammonium salts, for example: the tetramethylammonium cation, the trimethylbenzylammonium cation, the triethylbenzylammonium cation, the tetraethylammonium kation or trimethylethylammonium kation, and also the ammonium cation.

Preferred compounds of the formula I according to the invention are those wherein Ar is a phenyl group substituted in the ortho-position by Q, E is the nitrogen atom or the methine group, $R_1$ is hydrogen or methyl, $R_2$ is a $C_1$–$C_3$-alkyl, $C_1$–$C_3$-haloalkyl, $C_1$–$C_3$-alkoxy, $C_1$–$C_3$-haloalkoxy or $C_1$–$C_3$-alkylamino group, and Z is oxygen.

Ar is a phenyl group substituted in the ortho position by $C_1$–$C_4$-alkoxycarbonyl, E is the nitrogen atom or the methine group, $R_1$ is hydrogen or methyl, $R_2$ is a $C_1$–$C_3$-alkyl, $C_1$–$C_3$-haloalkyl, $C_1$–$C_3$-alkoxy, $C_1$–$C_3$-haloalkoxy or $C_1$–$C_3$-alkylamino group, and Z is oxygen.

Ar is a phenyl group substituted in the ortho position by $C_1$–$C_3$-haloalkoxy, E is the nitrogen atom or the methine group, $R_1$ is hydrogen or methyl, $R_2$ is a $C_1$–$C_3$-alkyl, $C_1$–$C_3$-haloalkyl, $C_1$–$C_3$-alkoxy, $C_1$–$C_3$-haloalkoxy or $C_1$–$C_3$-alkylamino group, and Z is oxygen.

Ar is a phenyl group substituted in the ortho position by halogen or nitro, E is the nitrogen atom or the methine group, $R_1$ is hydrogen or methyl, $R_2$ is a $C_1$–$C_3$-alkyl, $C_1$–$C_3$-haloalkyl, $C_1$–$C_3$-alkoxy, $C_1$–$C_3$-haloalkoxy or $C_1$–$C_3$-alkylamino group, and Z is oxygen.

Especially preferred are the compounds:
N-(4-cyclopropyl-6-methyl-pyrimidin-2-yl)-N'-(2-methoxycarbonylbenzenesulfonyl)urea,
N-(4-cyclopropyl-6-methoxy-1,3,5-triazin-2-yl)-N'-(2-methoxycarbonylbenzenesulfonyl)urea,
N-(4-cyclopropyl-6-ethoxy-1,3,5-triazin-2-yl)-N'-(2-difluoromethoxybenzenesulfonyl)urea, and
N-(4-cyclopropyl-6-ethoxy-1,3,5-triazin-2-yl)-N'-(2-methoxycarbonylbenzenesulfonyl)urea.

The compounds of the formula I are produced in an inert organic solvent.

According to one process, the compounds of the formula I are produced by reacting a sulfonamide of the formula II $$Ar-SO_2NH_2 \qquad (II),$$

wherein Ar has the meaning defined under the formula I, in the presence of a base, with an N-pyrimidinyl- or -triazinylcarbamate of the formula III

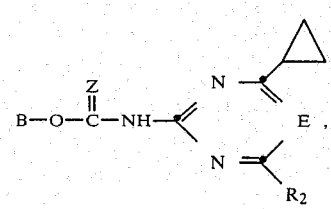

wherein E, $R_2$ and Z have the meanings defined under the formula I, and B—O— is a phenoxy, phenylalkoxy or alkoxy group which can be detached.

According to a second process, compounds of the formula I wherein R is hydrogen are produced by reacting a sulfonylisocyanate or sulfonylisothiocyanate of the formula IV $$Ar-SO_2-N=C=Z, \qquad (IV)$$

wherein Ar and Z having the meanings defined under the formula I, in the presence or absence of a base, with an amine of the formula V

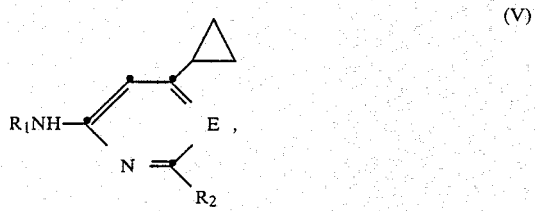

wherein E, $R_1$ and $R_2$ have the meanings defined under the formula I.

According to a further process, the compounds of the formula I are produced by reacting a sulfonamide of the formula II given above, in the presence or absence of a base, with an isocyanate or isothiocyanate of the formula VI

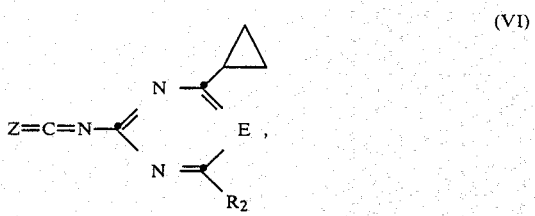

wherein E, $R_2$ and Z have the meanings defined under the formula I.

Furthermore, the compounds of the formula I can be produced by reacting an N-phenylsulfonylcarbamate of the formula VII $$Ar-SO_2NHCOO-B, \qquad (VII)$$

wherein Ar and B have the meanings defined in the foregoing, with an amine of the formula V given above.

The resulting ureas of the formula I can if required be converted, by means of amines, alkali metal hydroxides or alkaline-earth metal hydroxides or quaternary ammonium bases, into addition salts. This is effected for example by reaction with the equimolar amount of a base, and removal of the solvent by evaporation.

The starting materials of the formulae II, IV and VII are known and can be produced by known methods.

The cyclopropyl-pyrimidines and cyclopropyltriazines of the formula V, to which the intermediates of the formulae III and VI are strongly related, are in part novel. They and the production thereof likewise form subject matter of this invention.

2-Amino-4-cyclopropyl-6-methyl-pyrimidine is produced by treatment of cyclopropanecarboxylic acid or the anhydride thereof, in acetone, with boron trifluoride gas. There is formed cyclopropylbutane-1,3-dione, which is isolated, and then condensed, in an aqueous or alcoholic solution, with guanidine or with a guanidine salt, corresponding to the reaction pattern

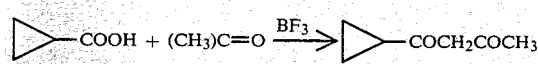

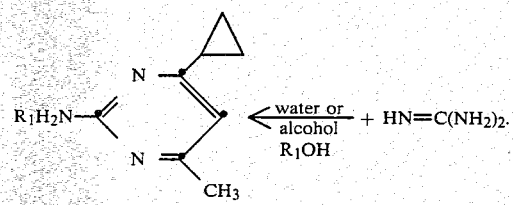

This compound can be reacted directly with an arylsulfonylisocyanate, or it can before the reaction be converted, in a known manner, into an isocyanate or into a carbamic acid ester.

2-Amino-4-cyclopropyl-6-hydroxy-pyrimidine is obtained by reaction of a cyclopropylcarboxylic acid halide, for example, the chloride or bromide, with 2,2-dimethyl-4,6-dioxo-dioxane (malonic acid-acetonacetal) in a basic solvent, for example in pyridine. There is formed 2,2-dioxane-4,6-dioxy-5-cyclopropylcarbonyl-dioxane, which is cleaved in water or in boiling alcohol to give cyclopropyloxo-acetic acid and an ester thereof, respectively. The stated compound is reacted with guanidine in water or in a lower alcohol to obtain 2-amino-4-cyclopropyl-6-hydroxy-pyrimidine, corresponding to the scheme:

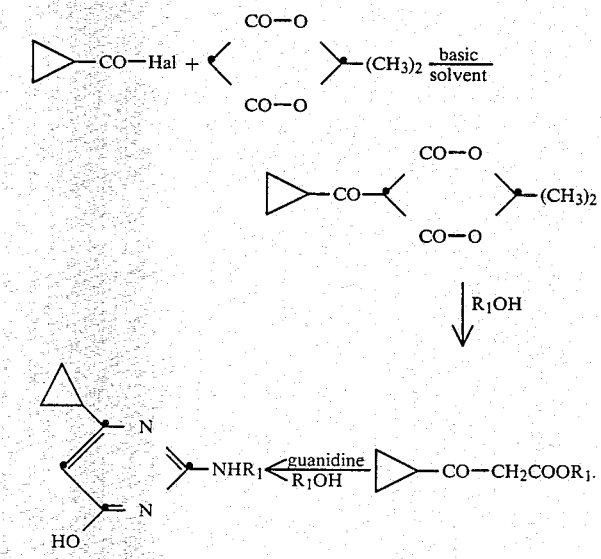

The hydroxyl group can be replaced by a halogen atom when this compound is treated with a halogenating agent, such as phosphorus oxychloride or phosphorus oxybromide. The halogen atom for its part can be replaced in a known manner by other substituents $R_2$, and the 2-amino-4-cyclopropylpyrimidines thus obtained can be reacted directly with an arylsulfonylisocyanate, or they can before the reaction be converted in a known manner into an isocyanate or into a carbamic acid ester.

2-Amino-4-cyclopropyl-6-trichloromethyl-1,3,5-triazine is produced by condensing 2 mols of trichloroacetonitrile with one mol of cyclopropylnitrile in the presence of hydrogen chloride to give 4-cyclopropyl-2,6-bis(trichloromethyl)-1,3,5-triazine, and then reacting this compound with one mol of ammonia or of an amine at temperatures of 0°–160° C. under normal pressure, corresponding to the reaction scheme:

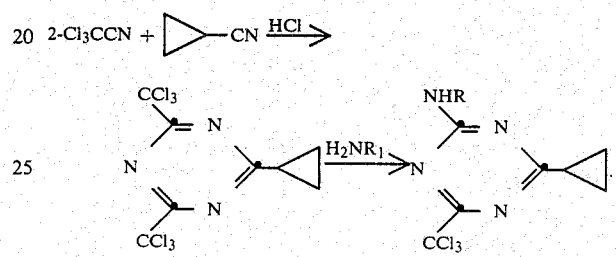

By reaction either of 4-cyclopropyl-2,6-bis-trichloromethyl-1,3,5-triazine or of 2-amino-4-cyclopropyl-6-trichloromethyl-1,3,5-triazine, in an absolute organic solvent, with at least the molar amount of an alkanol $R_2OH$ or of the alkali salt thereof, there is obtained the corresponding 2-amino-4-cyclopropyl-6-alkoxy-1,3,5-triazines of the formula V or 2-cyclopropyl-4,6-bis(alkoxy)-1,3,5-triazines, which can be converted, for example at higher temperatures 40°–140° C. and under pressure, with at least the molar amount of amine to give 2-amino-4-cyclopropyl-6-alkoxy-1,3,5-triazine. The 2-amino-4-cyclopropyl-1,3,5-triazines thus obtained can be reacted directly with an arylsulfonylisocyanate, or they can be converted by reaction in a known manner into an isocyanate or into a carbamic acid ester.

2-($\gamma$-Chloropropyl)-4,6-bis-(trichloromethyl)-1,3,5-triazine is obtained in an analogous manner by condensation of 2 mols of trichloroacetonitrile and one mol of $\gamma$-chlorobutyronitrile in the presence of hydrogen chloride. This compound can be reacted with the molar amount of amine $H_2NR_1$ at 0°–160° C. under normal pressure to give 2-amino-4-($\gamma$-chloropropyl)-6-trichloromethyl-1,3,5-triazine, which is converted with an alkali alcoholate in a suitable solvent at 0°–200° C. into 2-amino-4-cyclopropyl-6-alkoxy-1,3,5-triazine, and then further processed with an arylsulfonic acid isocyanate or -carbamic acid radical to obtain the desired urea of the formula I.

These reactions to compounds of the formula I are advantageously performed in aprotic, inert organic solvents, such as methylene chloride, tetrahydrofuran, acetonitrile, dioxane and toluene.

The reaction temperatures are preferably between −20° and +120° C. The reactions proceed in general slightly exothermically, and can be performed at room temperature. For the purpose of shortening the reaction time or of initiating the reaction, heat is advantageously applied for a short time up to the boiling point of the reaction mixture. The reaction times can be shortened also by the addition of a few drops of a base or isocyanate as a reaction catalyst.

The final products can be isolated by concentration by evaporation and/or by evaporating off the solvent, and purified by recrystallisation or by trituration of the solid residue in solvents in which they do not readily dissolve, such as ethers, aromatic hydrocarbons or chlorinated hydrocarbons.

The active substances of the formula I are stable compounds, and the handling of them requires no special safety measures.

In low applied amounts, which as a rule are from 0.01 to 1 kg per hectare, the compounds of the formula I are distinguished by good selective-growth retarding and selective-herbicidal properties, which render them excellently suitable for use in crops of cultivated plants, especially in crops of cereals, cotton, soya-bean, colza, maize and rice. It is also possible in some cases to destroy weeds which could be dealt with hitherto only by the application of total herbicides.

The mode of action of these active substances is unusual. Many are capable of being translocated, that is to say, they are taken up by the plant and transported to other locations, where they produce the desired effect. It is thus possible for example by surface treatment of perennial weeds to destroy them at their roots. The novel compounds of the formula I are effective in applied amounts which are very small compared with the amounts required to obtain the same effect using other herbicides and plant-growth regulators.

The compounds of the formula I also have excellent properties for regulating, especially reducing, plant growth. Both monocotyledons and dicotyledons are impaired in their growth.

Thus, for example, the leguminosae frequently planted as cover crops in agriculture in tropical regions can be selectively inhibited in their growth by the compounds of the formula I, the result being that soil erosion between the cultivated plants is prevented, without the cover crops being able to compete with the main cultivated crop.

Furthermore, the compounds of the formula I are suitable for preventing the sprouting of stored potatoes. Shoots frequently form on potatoes being stored during the winter, and the shoots cause shrinkage, loss in weight and rotting.

With larger applied amounts of active substance, all the tested plants were impaired in their development to the extent that they died.

The invention relates also to herbicidal and plant-growth-regulating compositions containing a novel active ingredient of the formula I, and also to processes for the pre- and post-emergence controlling of weeds, and for the reduction in growth of monocotyledonous and dicotyledonous plants, particularly that of grasses, tropical cover crops and side shoots of tobacco plants.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of compositions, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salts of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications: "Mc Cutcheon's Detergents and Emulsifiers Annual" MC Publishing Corp., Ridgewood, N.J., 1979; and Sisley and Wood, "Encyclopedia of Surface Active Agents", Chemical Publishing Co., Inc. New York, 1964.

The agrochemical preparations contain as a rule 0.1 to 95%, especially 0.1 to 80%, of active ingredient of the formula I, 1 to 99.9% of a solid or liquid additive, and 0 to 25%, particularly 0.1 to 25%, of a tenside.

Preferred formulations are made up in particular as follows (%=percent by weight):

| Emulsifiable concentrates | | |
|---|---|---|
| active ingredient | 1 to 20%, | preferably 5 to 10% |
| surface active agent: | 5 to 30%, | preferably 10 to 20% |
| liquid carrier: | 50 to 94%, | preferably 70 to 85% |
| Dusts | | |
| active ingredient: | 0.1 to 10%, | preferably 0.1 to 1% |
| solid carrier: | 99.9 to 90%, | preferably 99.9 to 99% |
| Suspension concentrates | | |
| active ingredient: | 5 to 75%, | preferably 10 to 50% |
| water: | 94 to 25%, | preferably 90 to 30% |
| surface-active agent: | 1 to 40%, | preferably 2 to 30% |
| Wettable powders | | |
| active ingredient: | 0.5 to 90%, | preferably 1 to 80% |
| surface-active agent: | 0.5 to 20%, | preferably 1 to 15% |
| solid carrier: | 5 to 95%, | preferably 15 to 90% |
| Granulates | | |
| active ingredient: | 0.5 to 30%, | preferably 3 to 15% |
| solid carrier: | 99.5 to 70%, | preferably 97 to 85% |

Whereas commercial products are preferably in the form of concentrated compositions, the compositions employed by the end-user are as a rule diluted. The preparations can for application be diluted down to 0.001% of active ingredient. The applied amounts are usually 0.001 to 10 kg, preferably 0.025 to 5, kg of active substance per hectare.

The compositions can also contain additives such as stabilisers, antifoaming agents, viscosity regulators, binders and adhesives, as well as fertilisers or other active substances for obtaining special effects.

In the following Examples, the temperatures are given in degrees Centigrade (°C.), and pressures in millibars (mb).

EXAMPLE 1

Production of 2-cyclopropyl-4,6-bis-trichloromethyl-1,3,5-triazine (intermediate)

760 g of trichloroacetonitrile are cooled to −15° C., and hydrogen chloride gas is blown through the solution until saturation is attained. There are then slowly added, with cooling and introduction of hydrogen chloride gas, 230 g of cyclopropylnitrile in such a manner that the temperature does not exceed −10° C. The cooling bath is subsequently removed and the reaction mixture is stirred at room temperature until the temperature rises to 15° C. There commences from 10° C. upwards, with a moderately exothermic reaction, the splitting-off of hydrogen which, after 20 hours' stirring at 15°–20° C., has finally finished.

1.5 liters each of ether and hexane are added to the reaction mixture; the whole is then thoroughly stirred and afterwards filtered. The filtrate is concentrated by evaporation; the residue is boiled up in 700 ml of hexane, filtration is again performed and the filtrate is once more concentrated by evaporation. The residue is recrystallised from methanol to thus obtain 350 g of the above triazine, m.p. 100°–102° C.

EXAMPLE 2

Production of 2-amino-4-cyclopropyl-6-trichloromethyl-1,3,5-triazine 71.2 g of 2-cyclopropyl-4,6-bis-trichloromethyl-1,3,5-triazine are dissolved in 70 ml of tetrahydrofuran, and at room temperature are added, with stirring, 300 ml of a concentrated aqueous ammonia solution. The reaction mixture is stirred for 30 minutes; it is then diluted with water, and the formed emulsion is extracted with ether. The ether phases are collected, dried, filtered and subsequently concentrated by evaporation. The residue crystallises and there remain 48 g of the crystalline title product, m.p. 111°–114° C.

EXAMPLE 3

Production of 2-cyclopropyl-4-methoxy-6-trichloromethyl-1,3,5-triazine

To a solution of 48 g of 2-cyclopropyl-4,6-bis-(trichloromethyl)-1,3,5-triazine in 200 ml of MeOH are added, with stirring, 4.9 g of sodium methylate, and the mixture is stirred for 1 hour at room temperature; it is then filtered and the filtrate is evaporated to dryness. The yield is 28.5 g of the title compound as a light-red oil, which solidifies after some time, m.p. 49°–51° C.

EXAMPLE 4

Production of 2-cyclopropyl-4,6-dimethoxy-1,3,5-triazine (intermediate)

8.1 g of sodium methylate are added to a solution of 71.2 g of 2-cyclopropyl-4,6-bis-(trichloromethyl)-1,3,5-triazine in 200 ml of methanol, and stirring is maintained for 5 hours at room temperature. The solution is then evaporated to dryness, and the residue is stirred up with 200 ml of ether. The resulting suspension is filtered and the filtrate is concentrated by evaporation. The residue crystallises, and is recrystallised from ether/hexane. The yield is 35.7 g of the above triazine, m.p. 68°–70° C.

EXAMPLE 5

Production of 2-cyclopropyl-4-amino-6-methoxy-1,3,5-triazine (intermediate)

To a solution of 10.8 g of sodium methylate in 50 ml of methanol are added 28.9 g of 2-amino-4-(3-chloropropyl)-6-trichloromethyl-1,3,5-triazine, and the mixture is stirred at 60° C. for 80 minutes. The formed suspension is filtered under suction, diluted with 250 ml of water, and extracted 3 times with 200 ml of ethylene chloride each time. The organic phases are dried, filtered, and concentrated by evaporation. The oil which remains is purified through a silica gel column, the eluant used being methylene chloride/ether (3:1). The eluant is evaporated off to leave 2.1 g of the title product, which is recrystallised from ether/chloroform, m.p. 158°–159° C.

EXAMPLE 6

Production of 2-amino-4-cyclopropyl-6-methoxy-1,3,5-triazine (intermediate)

Gaseous ammonia is blown through a solution of 5 g of 2-cyclopropyl-4,6-dimethoxy-1,3,5-triazine in 30 ml of methanol at room temperature until saturation is reached. The solution is then stirred in a bomb tube (autoclave) at 140° C. for 1 hour; it is subsequently cooled, and the reaction mixture is filtered to thus obtain 0.5 g of the title product as light-brown crystals, m.p. 156°–157° C.

EXAMPLE 7

Production of 2-amino-4-cyclopropyl-6-methoxy-1,3,5-triazine (intermediate)

5 ml of concentrated aqueous ammonia are added to a solution of 1 g of 2-cyclopropyl-4-methoxy-6-trichloromethyl-1,3,5-triazine in 3 ml of tetrahydrofuran; the whole is placed into a bomb tube and heated at 80° C. for 30 minutes. The mixture is cooled and then filtered; the filter residue is dissolved in 30 ml of methylene chloride, and the solution is dried over magnesium sulfate, and concentrated by evaporation. The residue crystallises to leave 0.4 g of white crystals, m.p. 157°–158° C.

EXAMPLE 8

Production of 2-amino-4-(3-chloropropyl)-6-trichloromethyl-1,3,5-triazine (intermediate)

102.3 g of 2-(3-chloropropyl)-4,6-bis-(trichloromethyl)-1,3,5-triazine are dissolved in 100 ml of tetrahydrofuran, and to this solution are added, whilst it is being stirred at room temperature, 400 ml of concentrated aqueous ammonia solution. After 30 minutes are added 500 ml of water, and the reaction mixture is extracted twice with 100 ml of ether each time. The ether phases are dried over magnesium sulfate, filtered, and concentrated by evaporation to yield 68.3 g of the title product as light-brown oil.

EXAMPLE 9

Production of 2-(3-chloropropyl)-4,6-bis-(trichloromethyl)-1,3,5-triazine (intermediate)

Gaseous hydrogen chloride is blown through a solution of 103 g of 4-chlorobutyronitrile in 298 g of trichloroacetonitrile at a temperature of −20° C. until saturation is reached. The mixture is then slowly warmed to room temperature with stirring, in the course of which only a relatively small evolution of gas results and a crystalline precipitate occurs. One liter of toluene is added and the reaction mixture is stirred at 85° C. until no further HCl gas evolves. Stirring is then ceased and the mixture is allowed to cool; the clear solution is decanted from the sludge which has settled. The solution is concentrated by evaporation, and the oil remaining is distilled under high vacuum to thus obtain 294 g of the title compound; b.p. 150°–160° C./0.2 mbar; refractive index $n_D^{27}$: 1.5498.

EXAMPLE 10

Production of 2-amino-4-cyclopropyl-6-methoxy-1,3,5-triazine (intermediate)

25.3 g of 2-amino-4-cyclopropyl-6-trichloromethyl-1,3,5-triazine are added to a solution of 10.8 g of sodium methylate in 50 ml of methanol, and the mixture is stirred at 60° C. for 80 minutes. There are added 300 ml of water, and the formed suspension is filtered. The filter residue is suspended twice in 100 ml of acetyl acetate each time, and again filtered. The organic phases are collected, dried over magnesium sulfate and concentrated by evaporation to thus obtain an oil, which crystallises when stirred up in ether. The yield is 6.7 g of the title compound, m.p. 158°–159° C.

In a manner analogous to that of these Examples, there are produced the following triazine starting products:

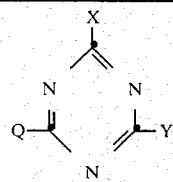

| Q | X | Y | Physical data | |
|---|---|---|---|---|
| CCl₃ | cyclopropyl | CCl₃ | m.p. 100–102° C. | Ex. 1 |

-continued

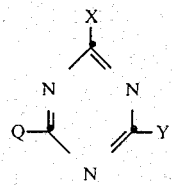

| Q | X | Y | Physical data | |
|---|---|---|---|---|
| NH$_2$ | cyclopropyl | CCl$_3$ | m.p. 114–116° C. | Ex. 2 |
| OCH$_3$ | cyclopropyl | CCl$_3$ | m.p. 49–51° C. | Ex. 3 |
| CH$_3$ | cyclopropyl | CH$_3$ | m.p. 68–70° C. | Ex. 4 |
| NH$_2$ | cyclopropyl | OCH$_3$ | m.p. 158–159° C. | Ex. 5, 6, 7, 10 |
| NH$_2$ | Cl C$_3$H$_6$— | CCl$_3$ | oil | Ex. 8 |
| CCl$_3$ | Cl C$_3$H$_6$— | CCl$_3$ | oil n$_D^{27}$: 1.5498 | Ex. 9 |
| NHC$_3$H$_{7n}$ | cyclopropyl | CCl$_3$ | oil | |
| NHC$_3$H$_{7n}$ | cyclopropyl | NHC$_2$H$_5$ | oil | |
| OCH$_3$ | cyclopropyl | OH | m.p. 160–164° C. | |
| NHC$_3$H$_{7n}$ | cyclopropyl | NH$_2$ | resin | |
| OC$_2$H$_5$ | cyclopropyl | CCl$_3$ | oil | |
| NHCH$_3$ | cyclopropyl | CCl$_3$ | m.p. 100–102° C. | |
| NHC$_2$H$_5$ | cyclopropyl | CCl$_3$ | m.p. 47–49° C. | |
| NHC$_3$H$_7$iso | cyclopropyl | CCl$_3$ | oil | |
| N(CH$_3$)$_2$ | cyclopropyl | CCl$_3$ | m.p. 59–61° C. | |
| NHCH$_3$ | cyclopropyl | OCH$_3$ | | |
| NHCH$_3$ | cyclopropyl | OC$_2$H$_5$ | | |
| NHCH$_3$ | cyclopropyl | OCH CF$_3$ | | |
| NH$_2$ | cyclopropyl | OC$_2$H$_5$ | | |
| NH$_2$ | cyclopropyl | OCH$_2$CF$_3$ | | |
| NH$_2$ | cyclopropyl | OC$_2$H$_4$Cl | | |
| NH$_2$ | cyclopropyl | OC$_2$H$_4$OCH$_3$ | | |
| NH$_2$ | cyclopropyl | OCH(CH$_3$)$_2$ | | |
| NH$_2$ | cyclopropyl | SCH$_3$ | | |
| NH$_2$ | cyclopropyl | NHNHCH$_3$ | | |
| NH$_2$ | cyclopropyl | N(CH$_3$)NHCH$_3$ | | |
| NH$_2$ | cyclopropyl | NHCOCH$_3$ | | |
| NH$_2$ | cyclopropyl | NH$_2$ | | |

EXAMPLE 11

Production of 1-cyclopropylbutane-1,3-dione (intermediate)

Boron trifluoride gas is introduced for one hour at 40° C. into a mixture of 191 g of cyclopropanecarboxylic acid and 45 g of acetone. There is formed a black oily product, which is diluted with 800 ml of ether. The ether phase is then washed 4 times with 300 ml of water each time, and, with ice cooling, 30% sodium hydroxide solution is finally added until the pH value is ~9. The ether layer is separated, and the aqueous phase is extracted three times with 300 ml of ether each time. The ether phases are collected, dried over sodium sulfate, purified with active charcoal, filtered, and concentrated by evaporation. The oil which remains is purified by chromatography through a silica gel column with ether/hexane (1:3) as the eluant. The yield after removal of the solvent by evaporation is 22 g of the title compound as light-coloured oil; refractive index n$_D^{24}$: 1.488.

EXAMPLE 12

Production of 2-amino-4-cyclopropyl-6-methylpyrimidine (intermediate)

15 g of guanidine carbonate are added to a mixture of 10 g of 1-cyclopropyl-butane-1,3-dione and 150 g of water, and stirring is maintained at 95° C. for 5 hours. The mixture is then concentrated by evaporation to a volume of 50 ml, and the cooled aqueous concentrate is extracted three times with 100 ml of ethylene chloride each time. The organic phase is dried over magnesium sulfate and concentrated by evaporation. The residue crystallises to thus yield 5 g of the title compound, m.p. 113°–115° C.

EXAMPLE 13

Production of N-(4-cyclopropyl-6-methylpyrimidin-2-yl)-N'-(2'-methoxycarbonylbenzenesulfonyl) urea

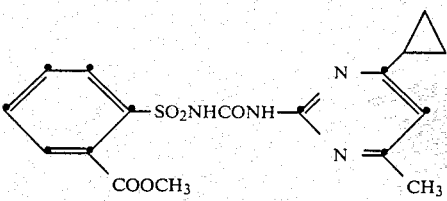

2.4 g of 2-methoxycarbonyl-benzenesulfonyl-isocyanate are added to a mixture of 1 g of 2-amino-4-cyclopropyl-6-methylpyridine in 7 ml of ether and 7 ml of ethylene chloride, and the mixture is stirred for 14 hours at room temperature. The occurring precipitate is filtered off to thus obtain 2.2 g of the above urea, m.p. 173°–175° C.

EXAMPLE 14

Production of N-(4-cyclopropyl-6-methoxy-1,3,5-triazin-2-yl)-N'-(2-methoxycarbonylbenzenesulfonyl)urea

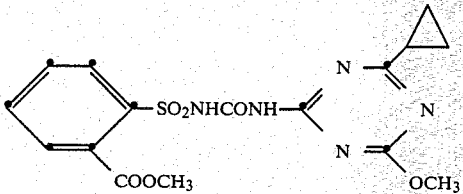

2.1 g of 2-methoxycarbonylbenzenesulfonylisocyanate are added with stirring, under a nitrogen atmosphere, to a solution of 1.3 g of 2-amino-4-cyclopropyl-6-methoxy-1,3,5-triazine in 10 ml of CH$_2$Cl$_2$. A slight exothermic reaction occurs, which soon however subsides. Stirring is maintained for 14 hours at room temperature, and the solution is then caused to crystallise by the addition of ether. The precipitate is filtered off and dried. The yield is 2.3 g of the above urea, which melts at 166°–168° C.

EXAMPLE 15

Production of N-(4-cyclopropyl-6-trichloromethyl-1,3,5-triazin-2-yl)-N'-(2-difluoromethoxybenzenesulfonyl)urea

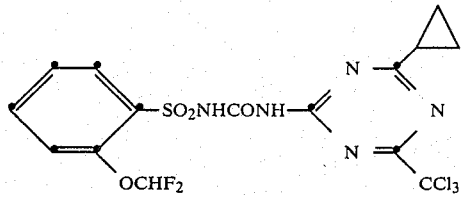

2.7 g of 2-difluoromethoxybenzenesulfonylisocyanate are added to a solution of 2.54 g of 2-amino-4-cyclopropyl-6-trichloromethyl-1,3,5-triazine, and the whole is stirred at room temperature for 14 hours. Hexane is then added until the reaction product precipitates. Filtration is carried out and the filtration residue is dried to thus obtain 3 g of the above urea, which melts at 103°–105° C.

EXAMPLE 16

Production of N-(4-cyclopropyl-6-methoxy-1,3,5-triazin-2-yl)-N'-(2-difluoromethoxybenzenesulfonyl)urea

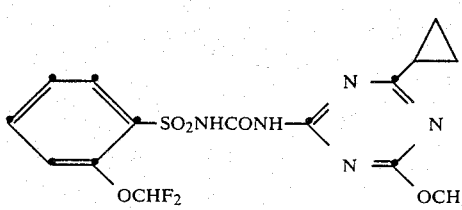

3.75 g of 2-difluoromethoxybenzenesulfonylisocyanate are added to a solution of 2.5 g of 2-amino-4-cyclopropyl-6-methoxy-1,3,5-triazine in 15 ml of methylene chloride, and the mixture is stirred for 70 hours at room temperature. It is then concentrated by evaporation, and 25 ml of ether are added to the residue. A crystalline precipitate occurs, which is filtered off. The yield is 4.7 g of the above urea, which melts at 121°–124° C.

EXAMPLE 17

The compound of Example 16 can be produced also as follows:

A solution of 0.54 g of NaOCH$_3$ in 1.26 g of methanol is added to a solution of 0.9 g of N-(4-cyclopropyl-6-trichloromethyl-1,3,5-triazin-2-yl)-N'-(2-difluoromethoxybenzenesulfonyl)urea (Example 15), and stirring is maintained at 50° C. for one hour. The reaction mixture is then poured into 100 ml of water; the whole is acidified with 10% aqueous hydrochloric acid to pH 1, and extracted four times with 50 ml of methylene chloride each time. The organic phases are dried over magnesium, filtered, and concentrated by evaporation. There remains an oil which, after trituration in ether, crystallises. The crystals are recrystallised in ether to thus obtain 0.66 g of the above urea, which melts at 122°–124° C.

The following sulfonylureas are produced in a manner analogous to that of these Examples:

| No. | Q | $R_1$ | $R_2$ | E | Melting point (°C.) |
|---|---|---|---|---|---|
| 1 | COOCH$_3$ | H | OCH$_3$ | N | 166–168° Example 14 |
| 2 | COOCH$_3$ | H | CCl$_3$ | N | 162° decomp. |
| 3 | Cl | H | OCH$_3$ | N | 161–164° |
| 4 | OCHF$_2$ | H | OCH$_3$ | N | 121–124° Ex. 16,17 |
| 5 | COOCH$_3$ | H | NHC$_3$H$_{7n}$ | N | 187–188° |
| 6 | NO$_2$ | H | OCH$_3$ | N | 179–182° |
| 7 | COOCH$_3$ | H | OC$_2$H$_5$ | N | 154–156° |
| 8 | OCH$_3$ | H | OCH$_3$ | N | 142–146° |
| 9 | OCHF$_2$ | H | CCl$_3$ | N | 103–105° |
| 10 | OCHF$_2$ | H | OC$_2$H$_5$ | N | 143–144° |
| 11 | NO$_2$ | H | OC$_2$H$_5$ | N | 182–184° |
| 12 | OCH$_3$ | H | OC$_2$H$_5$ | N | 149–151° |
| 13 | COOCH$_3$ | CH$_3$ | OCH$_3$ | N | 149–151° |
| 14 | OCHCF$_2$ | CH$_3$ | OCH$_3$ | N | 118–120° |
| 15 | OCH$_3$ | CH$_3$ | OCH$_3$ | N | 121–123° |
| 16 | COOCH$_3$ | CH$_3$ | CCl$_3$ | N | 133–135° |
| 17 | OCHF$_2$ | H | CCl$_3$ | N | 138–140° Ex. 15 |
| 18 | OCHF$_2$ | H | Cl | CH | |
| 19 | COOCH$_3$ | H | CH$_3$ | CH | 173–175° Ex. 13 |
| 20 | OCHF$_2$ | H | CH$_3$ | CH | 168–169° |
| 21 | OCH$_3$ | H | CH$_3$ | CH | 160–162° |
| 22 | NO$_2$ | H | CH$_3$ | CH | 153–157° |
| 23 | OCHF$_2$ | H | NHC$_3$H$_7$iso | N | 233–236° |
| 24 | Cl | H | NHC$_3$H$_7$iso | N | 209–211° |
| 25 | OC$_2$H$_4$OCH$_3$ | H | OCH$_3$ | N | 130–132° |
| 26 | COOCH$_3$ | H | NHC$_3$H$_7$iso | N | 210–212° |
| 27 | OCH$_3$ | H | NHC$_3$H$_7$iso | N | 202–205° |
| 28 | NO$_2$ | H | NHC$_3$H$_7$iso | N | 211–215° |
| 29 | Cl | H | OH | CH | |
| 30 | NO$_2$ | H | OH | CH | |
| 31 | Cl | H | CH$_3$ | CH | |
| 32 | Cl | H | OCH$_3$ | CH | |
| 33 | Cl | H | OC$_2$H$_5$ | CH | |
| 34 | OCH$_3$ | H | OCH$_3$ | CH | |
| 35 | OCH$_3$ | H | OC$_2$H$_5$ | CH | |
| 36 | OCH$_3$ | H | OCH$_2$CF$_3$ | CH | |
| 37 | NO$_2$ | H | OCH$_3$ | CH | 201–203° |
| 38 | NO$_2$ | H | OC$_2$H$_5$ | CH | |
| 39 | NO$_2$ | H | OCH$_2$CF$_3$ | CH | |
| 40 | OC$_2$H$_4$OCH$_3$ | H | CH$_3$ | CH | |
| 41 | COOCH$_3$ | H | OCH$_3$ | CH | 176–178° |
| 42 | COOCH$_3$ | H | OC$_2$H$_5$ | CH | |
| 43 | COOCH$_3$ | H | OCH$_2$CF$_3$ | N | |
| 44 | COOCH$_3$ | H | OCH$_2$CF$_3$ | CH | |
| 45 | NO$_2$ | H | OCH$_2$CF$_3$ | N | |
| 46 | OCHF$_2$ | H | OCH$_2$CF$_3$ | N | |
| 47 | OCHF$_2$ | H | OCH$_3$ | CH | 170–172° |
| 48 | OCHF$_2$ | H | OC$_2$H$_5$ | CH | |
| 49 | OCHF$_2$ | H | OCH$_2$CF$_3$ | CH | |
| 50 | OC$_2$H$_4$OCH$_3$ | H | OC$_2$H$_5$ | N | |
| 51 | OC$_2$H$_4$OCH$_3$ | H | OCH$_2$CF$_3$ | N | |
| 52 | OC$_2$H$_4$OCH$_3$ | H | CH$_3$ | CH | |
| 53 | OC$_2$H$_4$OCH$_3$ | H | OCH$_3$ | CH | 178–181° |
| 54 | OC$_2$H$_4$OCH$_3$ | H | OC$_2$H$_5$ | CH | |
| 55 | OC$_2$H$_4$OCH$_3$ | H | OCH$_2$CF$_3$ | CH | |
| 56 | SCHF$_2$ | H | OCH$_3$ | N | |
| 57 | SCHF$_2$ | H | OC$_2$H$_5$ | N | |
| 58 | SCHF$_2$ | H | OCH$_2$CF$_3$ | N | |
| 59 | SCHF$_2$ | H | CH$_3$ | CH | |
| 60 | SCHF$_2$ | H | OCH$_3$ | CH | |
| 61 | SCHF$_2$ | H | OC$_2$H$_5$ | CH | |
| 62 | SCHF$_2$ | H | OCH$_2$CF$_3$ | CH | |

-continued

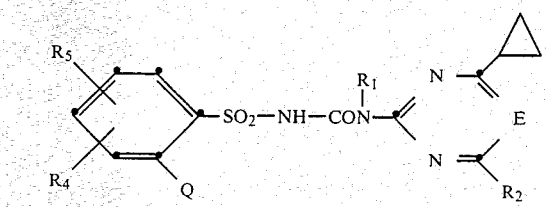

| No. | Q | R₁ | R₂ | E | Melting point (°C.) |
|---|---|---|---|---|---|
| 63 | COOCH₃ | H | Cl | CH | 190-193° |
| 64 | COOCH₃ | H | NHC₂H₅ | N | 208-210° |
| 65 | OCHF₂ | H | NHC₂H₅ | N | 230-232° |
| 66 | Cl | H | N(CH₃)₂ | N | 188-190° |
| 67 | OCHF₂ | H | NHCH₃ | N | 222-223° |
| 68 | OCHF₂ | H | N(CH₃)₂ | N | 160-162° |
| 69 | COOCH₃ | H | N(CH₃)₂ | N | 153-156° |
| 70 | Cl | H | NHC₂H₅ | N | 227-228° |
| 71 | NO₂ | H | NHC₂H₅ | N | 215-217° |
| 72 | Cl | H | SCH₃ | N | 120-125° |
| 73 | NO₂ | H | Cl | CH | 200° |
| 74 | OC₂H₄OCH₃ | H | Cl | CH | 153-154° |
| 75 | Cl | H | Cl | CH | 203-205° |
| 76 | OC(Cl)=CHCl | H | Cl | CH | 197-200° |
| 77 | OC(Cl)=CHCl | H | OCH₃ | CH | 212-215° |
| 78 | CO₂CH₃ | H | CH₃ | N | 158-160° |
| 79 | COOCH₃ | H | OCHF₂ | N | 140-142° |
| 80 | COOCH₃ | H | C₃H₅(cyclo) | CH | 178-180° |
| 81 | OCHF₂ | H | C₃H₅(cyclo) | CH | 153-155° |
| 82 | Cl | H | C₃H₅(cylco) | CH | 215-218° |
| 83 | F | H | C₃H₅(cyclo) | CH | 194-197° |
| 84 | CH₃ | H | C₃H₅(cyclo) | CH | 193-197° |
| 85 | OC(Cl)=CHCl | H | C₃H₅(cyclo) | CH | 214-215° |
| 86 | OCHF₂ | H | CH₃ | N | 152-153° |
| 87 | Cl | H | CH₃ | N | 155-157° |
| 88 | F | H | CH₃ | N | 159-161° |
| 89 | OC₂H₄Cl | H | CH₃ | N | 163-165° |
| 90 | OC(Cl)=CHCl | H | CH₃ | N | 172-174° |
| 91 | SCHF₂ | H | CH₃ | N | 178-180° |
| 92 | COOCH₃ | H | C₃H₅(cyclo) | N | 186-188° |
| 93 | OCHF₂ | H | C₃H₅(cyclo) | N | 120-125° |
| 94 | Cl | H | C₃H₅(cyclo) | N | 195-197° |
| 95 | F | H | C₃H₅(cyclo) | N | 174-176° |
| 96 | OCH₂CH₂Cl | H | C₃H₅(cyclo) | N | 178-180° |
| 97 | O(Cl)=CHCl | H | C₃H₅(cyclo) | N | 206-209° |
| 98 | SCHF₂ | H | C₃H₅(cyclo) | N | 165-168° |
| 99 | OCHF₂ | H | CH₂OCH₃ | N | 109-112° |
| 100 | Cl | H | CH₂OCH₃ | N | 172-175° |
| 101 | F | H | CH₂OCH₃ | N | 132-136° |
| 102 | OCH₂CH₂Cl | H | CH₂OCH₃ | N | 142-146° |
| 103 | OC₂H₄OCH₃ | H | CH₂OCH₃ | N | 129-132° |
| 104 | COOCH₃ | H | C₂H₅ | N | 168-170° |
| 105 | OCHF₂ | H | C₂H₅ | N | 106-109° |
| 106 | Cl | H | C₂H₅ | N | 190-193° |
| 107 | F | H | C₂H₅ | N | 156-158° |
| 108 | OCH₂CH₂Cl | H | C₂H₅ | N | 163-167° |
| 109 | OCH₂CH₂Cl | H | C₂H₅ | N | 136-138° |
| 110 | SCHF₂ | H | OCH₃ | N | 163-165° |
| 111 | OC₂H₄Cl | H | OCH₃ | N | 155-158° |
| 112 | Cl | H | OC₂H₅ | N | 139-142° |
| 113 | OCH₂CH₂Cl | H | OC₂H₅ | N | 152-155° |
| 114 | OCH₂CH₂OCH₃ | H | OC₂H₅ | N | 132-135° |
| 115 | SCHF₂ | H | OC₂H₅ | N | 163-166° |
| 116 | COOCH₃ | H | OC₂H₅ | N | 136-139° |
| 117 | COOCH₃ | H | SCH₃ | CH | |
| 118 | COOCH₃ | H | OC₂H₅ | CH | |
| 119 | OCF₃ | H | OCH₃ | N | |
| 120 | OCF₃ | H | OC₂H₅ | N | |
| 121 | OCHF₂ | H | SCH₃ | CH | |
| 122 | NO₂ | H | SCH₃ | CH | |
| 123 | OCH₂CH₂Cl | H | SCH₃ | CH | |
| 124 | OCH₂CH₂Cl | H | SCH₃ | CH | |
| 125 | OC(Cl)=CHCl | H | SCH₃ | CH | |
| 126 | SCH₂OCH₃ | H | OCH₃ | N | |
| 127 | SCH₂OCH₃ | H | OC₂H₅ | N | |
| 128 | SCH₂CH=CH₂ | H | OCH₃ | N | |
| 129 | SCH₂CH=CH₂ | H | OC₂H₅ | N | |
| 130 | SCH₂CH=CH₂ | H | OCH₃ | CH | |

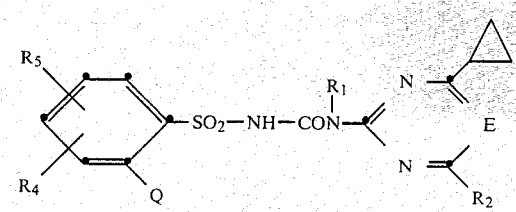

| No. | Q | R₁ | R₂ | E | Melting point (°C.) |
|---|---|---|---|---|---|
| 131 | SCH₂CH=CH₂ | H | OC₂H₅ | CH | |
| 132 | SCH₂OCH₃ | H | OCH₃ | CH | |
| 133 | SCH₂OCH₃ | H | OC₂H₅ | CH | |
| 134 | SCH₂C≡CH | H | OCH₃ | N | |
| 135 | SCH₂C≡CH | H | OC₂H₅ | N | |
| 136 | SCH₂C≡CH | H | OCH₃ | CH | |
| 137 | S(O)CH₂C≡CH | H | OCH₃ | N | |
| 138 | S(O)CH₂≡CCH | H | OCH₃ | CH | |
| 139 | SO₂CH₂C≡CH | H | OCH₃ | N | |
| 140 | SO₂CH₂C≡CH | H | OCH₃ | CH | |
| 141 | S(O)CH₂CH=CH | H | OCH₃ | N | |
| 142 | OCH₂CH=CH₂ | H | OCH₃ | N | |
| 143 | OCH₂C≡CH | H | OCH₃ | N | |
| 144 | NHCOCH₃ | H | OCH₃ | N | |
| 145 | CON(CH₃)₂ | H | OCH₃ | N | |
| 146 | SO₂CH₂C₆H₅ | H | OCH₃ | N | |
| 147 | SO₂CH₂C₆H₅ | H | OCH₃ | CH | |
| 148 | SO₂CH₂C₆H₅ | H | OC₂H₅ | CH | |
| 149 | SO₂CH₂C₆H₅ | H | OC₂H₅ | N | |

FORMULATION EXAMPLES

EXAMPLE 18

Formulation Examples for active ingredients of the formula I (% = percent by weight)

| (a) Wettable powder | (a) | (b) | (c) |
|---|---|---|---|
| active ingredient | 20% | 60% | 0.5% |
| sodium lignin sulfonate | 5% | 5% | 5% |
| sodium lauryl sulfate | 3% | — | — |
| sodium diisobutylnaphthalene sulfonate | — | 6% | 6% |
| octylphenolpolyethylene glycol ether (7-8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is well mixed with the additives and ground in a suitable mill. There are obtained wettable powders which can be diluted with water to give suspensions of the concentration desired.

| (b) Emulsion concentrate | (a) | (b) |
|---|---|---|
| active ingredient | 10% | 1% |
| octylphenolpolyethylene glycol ether (4-5 mols of ethylene oxide) | 3% | 3% |
| calcium dodecyl benzene sulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of the concentration desired can be obtained from this concentrate by dilution with water.

| (c) Dust | (a) | (b) |
|---|---|---|
| active ingredient | 0.1% | 1% |

-continued

| (c) Dust | (a) | (b) |
|---|---|---|
| talcum | 99.9% | — |
| kaolin | — | 99% |

Dusts ready for use are obtained by mixing the active-ingredient with the carriers, and grinding the mixture in a suitable mill.

| (d) Extruder granulate | (a) | (b) |
|---|---|---|
| active ingredient | 10% | 1% |
| sodium lignin sulfonate | 2% | 2% |
| carboxymethylcellulose | 1% | 1% |
| kaolin | 87% | 96% |

The active ingredient is mixed with the additives, and the mixture is then ground and moistened with water. It is extruded and subsequently dried in a stream of air.

| (e) Coated granulate | |
|---|---|
| active ingredient | 3% |
| polyethylene glycol (MG 200) | 3% |
| kaolin | 94% |

The finely ground active ingredient is uniformuly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenolpolyethylene glycol ether (15 mols of ethylene oxide) | 6% | 1% |
| sodium lignin sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the additives. There is thus obtained a suspension concentrate from which can be produced, by dilution with water, suspensions of the concentration required.

| (g) Salt solution | |
|---|---|
| active ingredient | 5% |
| isopropylamine | 1% |
| octylphenolpolyethylene glycol ether (78 mols of ethylene oxide) | 3% |
| water | 91% |

Biological Examples

EXAMPLE 19

Herbicidal action before emergence of the plants

Plant seeds are sown in flower pots (12–15 cm diameter) in a greenhouse. Th surface of the soil is treated immediately afterwards with an aqueous dispersion or solution of the active ingredients, the concentrations used being 500 g and 250 g, respectively, of active ingredient per hectare. The pots are then kept in the greenhouse at a temperature of 22°–25° C. with 50–70% relative humidity, and the test results are evaluated after 3 weeks. The condition of the plants is assessed according to the following scale of ratings:

9 plant has flourished as in the case of the untreated control plant, no damage,
8 very slight phytotoxic symptoms,
7 slight damage,
6 regenerable damage,
5 permanent damage,
4 stunted growth of plant,
3 severe damage,
2 very severe damage,
1 plant has died or has not germinated.

A selective herbicidal action exists where, with the same applied amount, the cultivated plant has ratings of 6–9 and the weeds have ratings of 1–4.

The results are summarised in the following.

| Compound No. | 1 | | 4 | | 6 | | 10 | | 13 | | 37 | |
|---|---|---|---|---|---|---|---|---|---|---|---|---|
| Applied amount g/ha | 500 | 250 | 500 | 250 | 500 | 250 | 500 | 250 | 500 | 350 | 500 | 350 |
| plant | | | | | | | | | | | | |
| wheat | 9 | 9 | 7 | 8 | 8 | 8 | 7 | 8 | 6 | 8 | 8 | 8 |
| *Alopecurus myosuroides* | 2 | 3 | 2 | 2 | 3 | 4 | 1 | 3 | 1 | 1 | 2 | 4 |
| *Echinochloa crus galli* | 3 | 4 | 4 | 4 | 4 | 4 | 3 | 4 | 1 | 2 | 2 | 2 |
| *Cyperus esculentus* | 3 | 4 | 3 | 4 | 3 | 4 | 2 | 3 | 1 | 1 | 1 | 1 |
| Abutilon sp. | 1 | 2 | 2 | 2 | 3 | 3 | 1 | 2 | 1 | 1 | 2 | 3 |
| *Xanthium spinosum* | 2 | 3 | 1 | 3 | 3 | 4 | 3 | 4 | 2 | 2 | 2 | 3 |
| *Chenopodium album* | 2 | 2 | 1 | 1 | 2 | 2 | 2 | 2 | 2 | 2 | 2 | 2 |
| *Ipomoea purpurea* | 2 | 2 | 2 | 3 | 2 | 2 | 2 | 2 | 2 | 2 | 2 | 2 |
| *Sinapis alba* | 1 | 1 | 2 | 2 | 2 | 2 | 2 | 2 | 2 | 2 | 2 | 2 |
| *Galium aparine* | 4 | 4 | 2 | 2 | 1 | 2 | 2 | 3 | 3 | 4 | 2 | 3 |
| *Viola tricolor* | 3 | 3 | 2 | 2 | 1 | 1 | 2 | 2 | 1 | 1 | 2 | 2 |

EXAMPLE 20

Herbicidal action after emergence of the plants (contact action)

A number of weeds and cultivated plants, both monocotyledons and dicotyledons, are sprayed in the 4- to 6-leaf stage with an aqueous active-ingredient dispersion in dosages of 4 kg of active substances per hectate, and are then kept at 24° to 26° C. with 45–60% relative humidity. The test results are evaluated 15 days after the treatment, and the state of the plants is assessed according to the scale of ratings used in the pre-emergence test.

The results are summarised in the following.

| Compound No. | 1 | | 3 | | 4 | | 6 | | 7 | | 8 | |
|---|---|---|---|---|---|---|---|---|---|---|---|---|
| Applied amount g/ha | 250 | 125 | 250 | 125 | 250 | 125 | 250 | 125 | 250 | 125 | 250 | 125 |
| plant | | | | | | | | | | | | |
| wheat | 9 | 9 | 9 | 9 | 8 | 9 | 9 | 9 | 7 | 8 | 8 | 9 |
| maize | 5 | 7 | 8 | 8 | 7 | 9 | 5 | 7 | 2 | 3 | 5 | 7 |
| Alopecurus myosuroides | 4 | 4 | 5 | 7 | 3 | 4 | 4 | 6 | 2 | 3 | 4 | 6 |
| Echinochloa crus galli | 8 | 8 | 8 | 9 | 8 | 9 | 7 | 8 | 4 | 4 | 2 | 6 |
| Cyperus esculentus | 4 | 4 | 3 | 4 | 3 | 3 | 3 | 4 | 3 | 3 | 4 | 6 |
| Abutilon sp. | 2 | 2 | 5 | 5 | 3 | 3 | 3 | 4 | 2 | 3 | 2 | 3 |
| Xanthium spinosum | 1 | 1 | 2 | 2 | 2 | 2 | 2 | 3 | 2 | 2 | 1 | 4 |
| Chenopodium album | 2 | 2 | 3 | 3 | 2 | 2 | 2 | 3 | 2 | 2 | 2 | 3 |
| Ipomoea purpurea | 4 | 4 | 3 | 4 | 3 | 4 | 3 | 4 | 3 | 4 | 3 | 5 |
| Sinapis alba | 2 | 3 | 2 | 3 | 2 | 2 | 2 | 2 | 2 | 2 | 2 | 3 |
| Galium aparine | 2 | 2 | 3 | 3 | 2 | 2 | 2 | 2 | 2 | 2 | 2 | 3 |
| Viola tricolor | 2 | 4 | 3 | 3 | 2 | 2 | 2 | 2 | 2 | 2 | 3 | 4 |

| | Verbindung No. | | | | | | | |
|---|---|---|---|---|---|---|---|---|
| | 10 | | 19 | | 41 | | 73 | |
| | Aufwandmenge g/ha | | | | | | | |
| | 250 | 125 | 250 | 125 | 250 | 125 | 250 | 125 |
| Pflanze | | | | | | | | |
| Weizen | 9 | 9 | 3 | 4 | 5 | 7 | 6 | 8 |
| Mais | 5 | 7 | 3 | 8 | 4 | 8 | 4 | 8 |
| Alopecurus myosuroides | 2 | 3 | 3 | 4 | 2 | 2 | 3 | 5 |
| Echinochloa crus galli | 4 | 6 | 2 | 3 | 4 | 5 | 3 | 4 |
| Cyperus esculentus | 3 | 5 | 3 | 4 | 3 | 4 | 4 | 5 |
| Abutilon sp. | 3 | 3 | 3 | 4 | 2 | 2 | 2 | 3 |
| Xanthium spinosa | 2 | 4 | 3 | 3 | 1 | 1 | 2 | 2 |
| Chenopodium album | 2 | 3 | 3 | 4 | 2 | 3 | 2 | 2 |
| Ipomoea purpurea | 4 | 4 | 4 | 4 | 4 | 5 | 4 | 4 |
| Sinapis alba | 2 | 3 | 3 | 3 | 3 | 4 | 3 | 3 |
| Galium aparine | 3 | 4 | 4 | 4 | 3 | 4 | 3 | 5 |
| Viola tricolor | 3 | 4 | 4 | 5 | 2 | 3 | 2 | 3 |

EXAMPLE 21

Reduction of sprouting on stored potatoes

A number of commercially available potatoes of the "Urgenta" variety, exhibiting no germination (sprouting), are washed and dried. The potatoes are afterwards each immersed for one minute in active-ingredient emulsions of varying concentration; they are then laid out on filter paper in plastics dishes, and stored at temperatures of 14° and 21° C. in darkness with 50% relative humidity, and an evaluation is made 34 days after application. At the same time the loss in weight of the tubers and the weight of the sprouts, compared with those values in the case of the untreated control specimens are determined. The compounds according to the invention brought about in this test a complete prevention of sprouting. The loss in weight of the potatoes was less than 10% of that of the control potatoes.

EXAMPLE 22

Reduction in growth of tropical leguminous cover crops

The test plants (centrosema plumieri and centrosema pubescens) are cultivated up to the fully grown stage, and then cut back to a height of 60 cm. After 7 days, the active substance is sprayed on in the form of an aqueous emulsion. The test plants are maintained at 70% relative humidity and with 6000 lux of artificial light, 14 hours per day, at temperatures of 27° C. by day and 21° C. by night. The test results are assessed 4 weeks after application of the emulsion. The new growth occurring compared with that on the control plants is estimated and weighed, and the phytotoxicity is evaluated. The plants treated with the active ingredients of the formula I show in this test a clear reduction in new growth (less than 20% of the new growth occurring on untreated control plants), without the test plants having suffered damage.

What is claimed is:

1. An N-(cyclopropyl-triazinyl-)-N'-(arylsulfonyl-)urea of the formula I

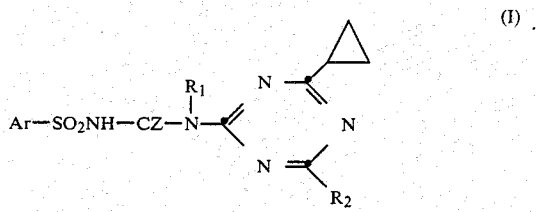

wherein Ar is a phenyl group

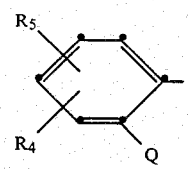

or a naphthyl group

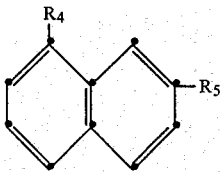

and

Q is a group X-A or $R_3$,

A is a $C_3$-$C_6$-alkynyl group, a $C_1$-$C_6$-alkyl group which is unsubstituted or substituted by halogen, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-haloalkoxy, $C_1$-$C_4$-haloalkylthio, $C_1$-$C_4$-haloalkylsulfinyl or $C_1$–$C_4$-haloalkylsulfonyl, or a $C_2$–$C_6$-alkenyl group which is unsubstituted or substituted by the groups given in the foregoing for $C_1$–$C_6$-alkyl, or A is a phenyl or benzyl group, X is oxygen, sulfur, or a sulfinyl or sulfonyl bridge, Z is oxygen or sulfur, $R_1$ is hydrogen, $C_1$–$C_4$-alkyl or $C_1$–$C_4$-alkoxy, $R_2$ is halogen, $C_1$–$C_3$-alkyl, $C_1$–$C_3$-haloalkyl, $C_1$–$C_3$-alkoxy, $C_1$–$C_3$-haloalkoxy, amino, $C_1$–$C_3$-alkylamino, di-($C_1$–$C_3$-alkyl)amino, $C_3$–$C_6$-cycloalkyl or $C_2$–$C_6$-alkoxyalkyl, $R_3$ is hydrogen, halogen, $C_1$–$C_5$-alkyl, $C_2$–$C_5$-alkenyl, $C_1$–$C_4$-haloalkyl, or a group —X—$R_6$, —COZ$R_{11}$, —NO$_2$ or —CO—NR$_8$R$_9$, —CN, —COR$_{10}$, —NR$_1$R$_7$ or —NR$_1$—COR$_{12}$, $R_4$ is hydrogen; $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, halogen, or alkoxyalkyl having at most 4 carbon atoms, $R_5$ is the same as $R_3$ but independent thereof, $R_6$ and $R_7$ are each $C_1$–$C_5$-alkyl, $C_2$–$C_5$-alkenyl or $C_2$–$C_6$-alkynyl, $R_8$ and $R_9$ independently of one another are each hydrogen, $C_1$–$C_5$-alkyl, $C_2$–$C_5$-alkenyl or $C_2$–$C_6$-alkynyl, $R_{10}$ is hydrogen, $C_1$–$C_4$-alkyl or $C_1$–$C_3$-haloalkyl, $R_{11}$ is hydrogen, $C_1$–$C_4$-alkyl, $C_1$–$C_3$-haloalkyl, $C_3$–$C_5$-alkenyl, $C_3$–$C_5$-alkynyl, phenyl or benzyl, and $R_{12}$ is the same as $R_1$ but independent thereof.

2. A compound according to claim 1, wherein Z is oxygen.

3. A compound of the formula I according to claim 2, wherein Ar is a phenyl group substituted in the orthoposition by Q, $R_1$ is hydrogen or methyl, and $R_2$ is a $C_1$–$C_3$-alkyl, $C_1$–$C_3$-haloalkyl, $C_1$–$C_3$-alkoxy, $C_1$–$C_3$-haloalkoxy or $C_1$–$C_3$-alkylamino group.

4. A compound of the formula I according to claim 3, wherein Ar is a phenyl group substituted in the orthoposition by $C_1$–$C_4$-alkoxycarbonyl.

5. A compound of the formula I according to claim 3, wherein Ar is a phenyl group substituted in the orthoposition by $C_1$–$C_3$-haloalkoxy.

6. A compound of the formula I according to claim 3, wherein Ar is a phenyl group substituted in the orthoposition by halogen or nitro.

7. N-(4-Cyclopropyl-6-methoxy-1,3,5-triazin-2-yl)-N'-(2-methoxycarbonylbenzenesulfonyl)urea according to claim 4.

8. N-(4-Cyclopropyl-6-ethoxy-1,3,5-triazin-2-yl)-N'-(2-difluoromethoxybenzenesulfonyl)urea according to claim 5.

9. A herbicidal and plant-growth-reducing composition which contains, as active ingredient, an effective amount of an N-phenylsulfonyl-N'-triazinyl-urea according to claim 1, together with a carrier.

10. A method of controlling undesirable plant growth, which method comprises applying thereto or to the locus thereof an effective amount of an N-(cyclopropyl-triazinyl)-N'-(arylsulfonyl)-urea according to claim 1.

11. A method of reducing plant growth, which method comprises applying thereto or to the locus thereof an effective amount of an N-(cyclopropyl-triazinyl)-N'-(arylsulfonyl)-urea according to claim 1.

12. A method for the pre- or post-emergence controlling of weeds in crops of cultivated plants, which method comprises applying thereto or to the locus thereof an effective amount of an N-(cyclopropyl-triazinyl)-N'-(arylsulfonyl)-urea according to claim 1.

13. A method of suppressing plant growth beyond the two-leaf stage, which method comprises applying before emergence of the plants an effective amount of an N-(cyclopropyl-triazinyl)-N'-(arylsulfonyl)-urea according to claim 1.

* * * * *